United States Patent [19]

Leka et al.

[11] 4,453,898

[45] Jun. 12, 1984

[54] DUAL-PISTON RECIPROCATING PUMP ASSEMBLY

[75] Inventors: George T. Leka, Trumbull; Roland C. Paradis, Bridgeport, both of Conn.

[73] Assignee: The Perkin-Elmer Corporation, Norwalk, Conn.

[21] Appl. No.: 446,137

[22] Filed: Dec. 2, 1982

Related U.S. Application Data

[60] Continuation of Ser. No. 189,547, Sep. 22, 1980, abandoned, which is a division of Ser. No. 014,514, Feb. 22, 1979, Pat. No. 4,260,342, which is a division of Ser. No. 820,592, Aug. 1, 1977, Pat. No. 4,173,437.

[51] Int. Cl.³ .................... F04B 39/00; F04B 27/02
[52] U.S. Cl. ...................................... 417/521; 417/426
[58] Field of Search ............... 417/539, 521, 522, 273, 417/426; 91/498, 499

[56] References Cited

U.S. PATENT DOCUMENTS

| | | | |
|---|---|---|---|
| 1,723,874 | 8/1929 | Lunge | 417/517 |
| 2,010,377 | 8/1935 | Sassen | 417/517 |
| 2,992,619 | 7/1961 | Nilges | 91/499 |
| 3,287,993 | 11/1966 | Lomicki | 91/498 |
| 3,323,461 | 6/1967 | Bonneff | 417/478 |
| 3,816,029 | 6/1974 | Bowen | 417/539 |
| 3,981,620 | 9/1976 | Abrahams | 417/42 |
| 4,105,371 | 8/1978 | Sauage | 417/273 |
| 4,195,970 | 1/1980 | Zalis | 417/474 |

FOREIGN PATENT DOCUMENTS

| | | | |
|---|---|---|---|
| 1800142 | 4/1970 | Fed. Rep. of Germany | 417/426 |
| 2446805 | 8/1976 | Fed. Rep. of Germany | 417/539 |
| 2608664 | 8/1977 | Fed. Rep. of Germany | 417/437 |
| 2706685 | 8/1978 | Fed. Rep. of Germany | 417/539 |
| 509039 | 7/1939 | United Kingdom | 417/539 |

Primary Examiner—William L. Freeh
Attorney, Agent, or Firm—F. L. Masselle; E. T. Grimes; R. A. Hays

[57] ABSTRACT

The invention is directed to a dual-piston reciprocating pump assembly which includes two opposed substantially identical reciprocating pumps, a housing within which the pumps are mounted, a cam mounted on a cam shaft which is driven through a coupling by a stepping motor, each of the pumps including a piston assembly comprising a piston body having a piston end, the other end of the piston body being in the form of a yoke which is mounted for reciprocating motion in the housing, a cam follower carried between the arms of the yoke for engaging the cam face of the cam, a cylinder head having a piston cylinder therein for receiving the piston end, the housing having an end opening for receiving said cylinder head, a guide bushing mounted in the cylinder head for facilitating the assembly of the piston end, an inner bearing bore for the piston end disposed adjacent the guide bushing, a high-pressure seal disposed adjacent the inner bearing bore, the piston end having substantial radial end play, and a piston spring mounted for urging the piston inwardly to maintain the cam follower in engagement with the cam face: according to one aspect of the invention, the cam face profile is shaped to synchronize the pistons for pumping and filling to minimize pressure pulsations and produce a substantially constant flow of fluid; according to another aspect of the invention, the cylinder head has an inlet passage extending outwardly from the piston cylinder and an inlet check valve is connected to this passage, an outlet passage extending outwardly from the piston cylinder, which is substantially axially offset with respect to the inlet passage along the center line of the piston cylinder to reduce the retention of trapped gas in the cylinder head and assists in obtaining a thorough flush of the cylinder head when changing solvents, and an outlet check valve connected to the outlet passage.

4 Claims, 12 Drawing Figures

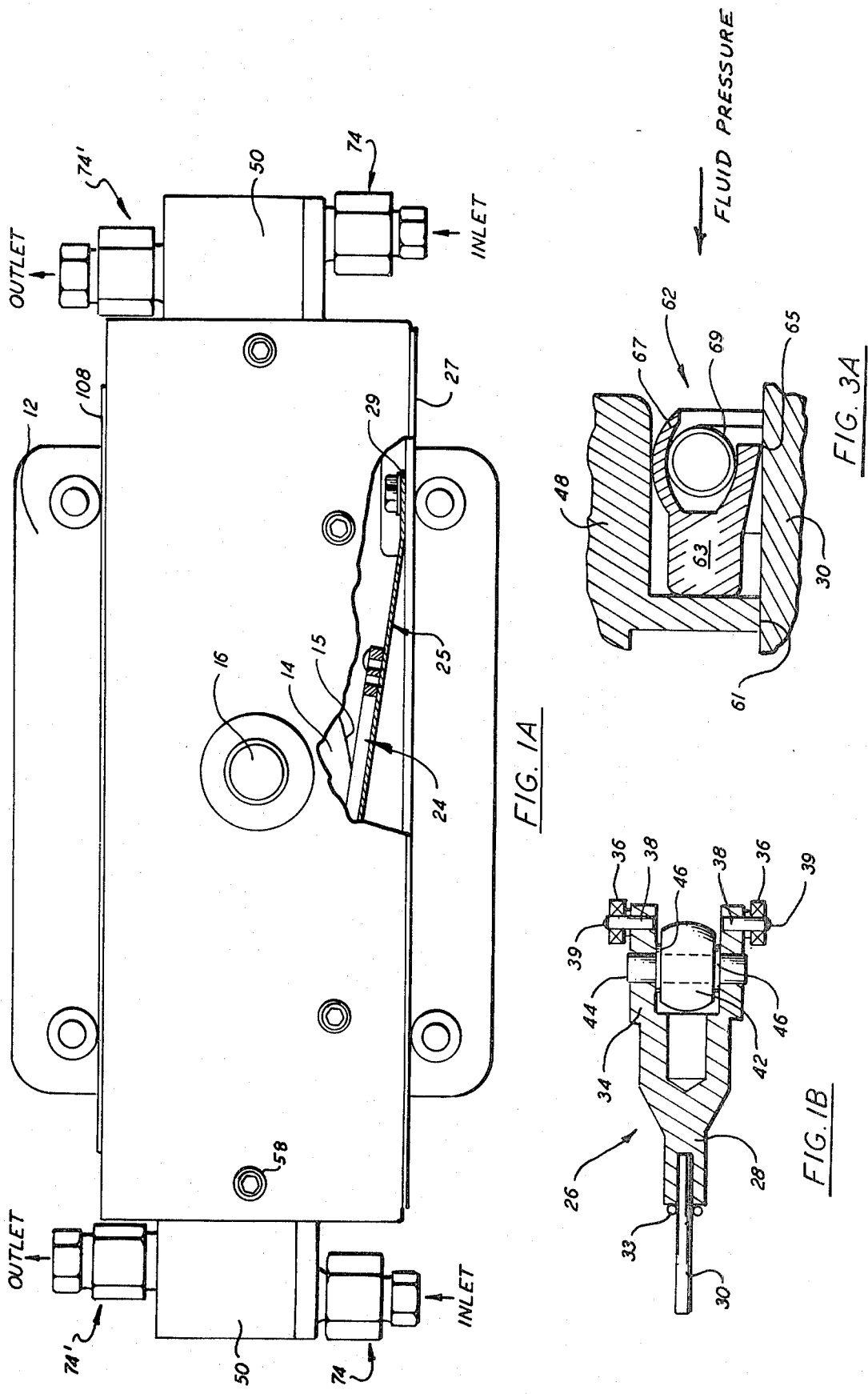

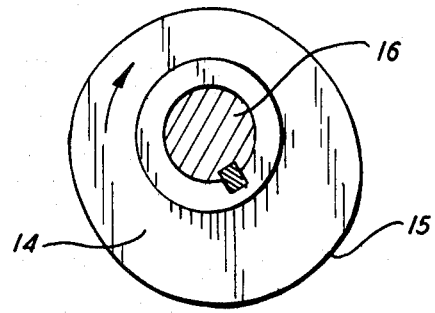

FIG. 4

| CAM ROTATION | FOLLOWER DISPLACEMENT EQUATION |
|---|---|
| 0° - 30° | $y = 4h \left(\frac{\theta}{60°}\right)^2$ |
| 30° - 180° | $y = h + \frac{(h_1-h)(\theta-30°)}{150°}$ |
| 180° - 210° | $y = 2h \left\{1 - 2\left[1 - \frac{(\theta-150°)}{60°}\right]^2\right\} + h_1 - h$ |
| 210° - 215° | $y = h_2$ DWELL (CONTINUOUS MAX. DISPLACEMENT) |
| 215° - 345° | $y = h_2 - \left\{\frac{h_2}{\pi}\left[\frac{\pi(\theta-215°)}{130°} - \frac{1}{2}\sin\frac{2\pi(\theta-215°)}{130°}\right]\right\}$ |
| 345° - 360° | $y = 0$ DWELL (CONTINUOUS NO DISPLACEMENT) |

FIG. 5

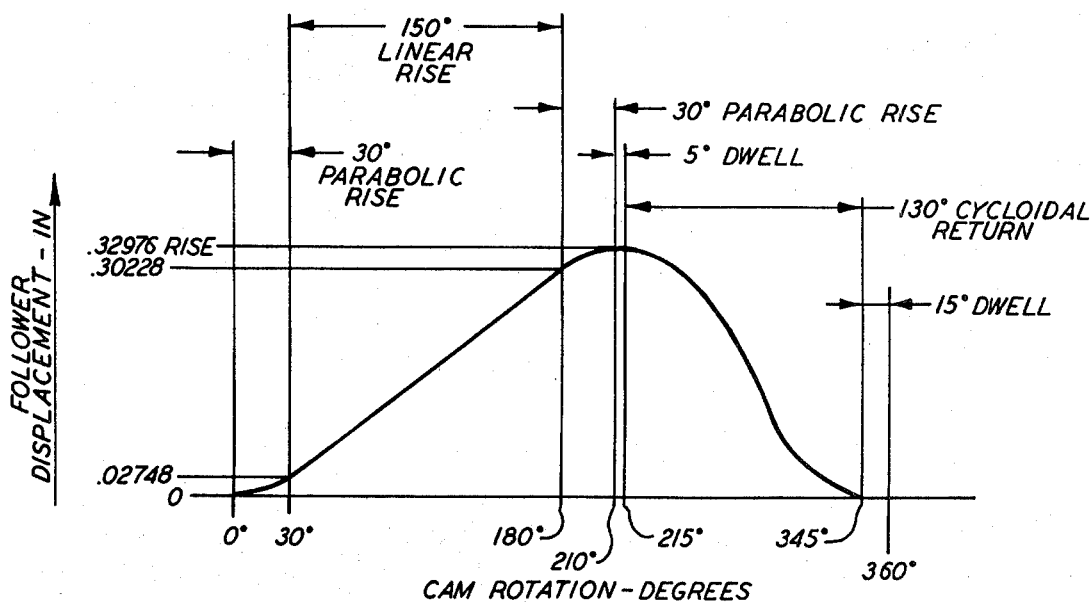

CAM FOLLOWER DISPLACEMENT DIAGRAM

FIG. 6

DUAL-PISTON RECIPROCATING PUMP ASSEMBLY

This application is a continuation of application Ser. No. 189,547, filed Sept. 22, 1980, now abandoned, which is a division of Ser. No. 014,514, filed Feb. 22, 1979, now U.S. Pat. No. 4,260,342, which is a division of Ser. No. 820,592, filed Aug. 1, 1977, now U.S. Pat. No. 4,173,437.

BACKGROUND OF THE INVENTION

This invention relates to dual-piston reciprocating pump assemblies. It is particularly adapted, among many other possible applications, for use in liquid chromatography systems. In such systems, reciprocating pumps are used to pump chromatographic solvents (mobile phase) through a liquid chromatography column. A sample, which is injected into the top of the column, will separate as it is carried through the column. After separation occurs, a detector, recorder and other components are used for quantative or qualitative sample analysis.

Heretofore, difficulties were encountered during cylinder head assembly and disassembly due to frequent breakage of the sapphire piston. Further, prior art reciprocating pumps tended to have excessive pressure pulsations and uneven flow characteristics during operation. Moreover, such prior art pumps frequently were of a relatively complicated design, employing many moving parts, which were subject to wear.

SUMMARY OF THE INVENTION

The basic and general object of the present invention is the provision of a new and improved dual-piston reciprocating pump assembly, which is an improvement over such prior art pump assemblies, as outlined hereinbefore.

To the accomplishment of the foregoing objectives, and additional objectives and advantages, which will become apparent as this description proceeds, the invention contemplates the provision of a dual-piston reciprocating pump assembly, which comprises two opposed substantially identical reciprocating pumps, a housing within which the pumps are mounted, and a cam mounted on a cam shaft which is driven through a coupling by a stepping motor. Each of the reciprocating pumps includes a piston assembly, comprising a piston body having a piston end, the other end of the piston body being in the form of a yoke which is mounted for reciprocating motion in the housing. A cam follower is carried between the arms of the yoke for engaging the cam face of the cam. A cylinder head is provided which has a piston cylinder therein for receiving the piston end, said housing having an end opening for receiving the cylinder head and bearing means are provided for the piston end. A guide bushing is mounted adjacent the bearing means for facilitating the assembly of the piston end. Further, means are provided for mounting a high-pressure seal adjacent the bearing means. The piston end has substantial radial end play which, in one form of the invention, is in the range of between about 0.052 inches to about 0.0728 inches, thereby minimizing the danger of breaking the sapphire piston during assembly and disassembly. The assembly further includes a piston spring, and means for mounting the spring for urging the piston inwardly to maintain said cam follower in engagement with the cam face.

According to one feature of the invention, dowel pins extend from the arms of the yoke, that carry ball bearings for mounting the piston body for reciprocating motion in the housing, said housing having longitudinally extending slots in which the ball bearings ride. The piston bearing dowel pins have spherical outer ends for transmitting the cam side component of force to the pump housing.

According to another feature of the invention, the bearing means in the cylinder head has a clearance of from about 0.0003 inches to about 0.00065 inches with respect to the sapphire piston end, and wherein the high-pressure seal is a high-pressure fluorocarbon seal.

According to still another feature of the invention, a glass cover is provided for the housing, whereby the operator can monitor the mechanical operation of the pump assembly.

According to one aspect of the invention, the cyinder head has an inlet passage extending outwardly from the piston cylinder, and an inlet check valve is connected to this inlet passage. An outlet passage extends outwardly from the piston cylinder, said outlet passage being substantially axially offset with respect to the inlet passage along the center line of the piston cylinder to reduce the retention of trapped gas and provide thorough flushing of the cylinder head. An outlet check valve is connected to the outlet passage.

In one form of the invention, the reciprocating pump assembly has a cylinder head with a piston cyinder disposed therein. The cylinder head has an inlet passage extending outwardly from the piston cylinder. An inlet check valve is provided which includes a concentric valve seat and an eccentric valve seat mounted in series with respect to each other. The concentric valve seat has a throughbore which is in alignment with the inlet passage, and the eccentric valve seat has a throughbore that is slightly off-set with respect to both the inlet passage and the throughbore in the concentric valve seat, but is in fluid flow communication therewith. The throughbore in the concentric valve seat has an enlarged portion adjacent the eccentric valve seat, and a first check valve ball is loosely mounted in this enlarged portion. The throughbore in the eccentric valve seat has an enlarged portion adjacent the cylinder head, and a second check valve ball is loosely mounted within the second enlarged portion. As a result, during piston cylinder refill, the first ball moves inwardly and rests against the face of the eccentric valve seat, and the second ball moves inwardly against the face of the cylinder head, to thereby provide fluid flow communication through the valve seats to the inlet passage in the cylinder head. During the pumping stroke, the pressure of the fluid urges the second ball outwardly until it covers the inlet of the throughbore in the eccentric valve seat and moves the first ball outwardly until it covers the throughbore in the concentric valve seat, to thereby prevent the flow of fluid through the check valve assembly. In addition, the cylinder head has an outlet passage extending outwardly from the piston cylinder, which is substantially axially offset with respect to the inlet passage along the center line of the piston cylinder. The outlet check valve comprises a check valve fitting adapted to receive a conventional pump outlet tube, said check valve fitting having an outlet passage in alignment with the outlet passage in the cylinder. A concentric valve seat is mounted adjacent the outlet passage in the cylinder head, and an eccentric valve seat is mounted in series with respect to the concentric valve seat. The concentric valve seat is provided with a throughbore which is in alignment with the outlet passages, and the eccentric valve seat has a throughbore that is slightly off-center with respect to the outlet passages, but is in fluid flow communication therewith. The throughbore in the concentric valve seat has an enlarged portion adjacent the eccentric valve seat and a first check valve ball loosely fits in this enlarged portion. The throughbore in the eccentric valve seat has an enlarged portion adjacent the check valve fitting, and a second check valve ball is loosely disposed within the second enlarged portion. As a result, during the piston cylinder refilling operation, the first ball moves inwardly until it covers the throughbore in the concentric valve seat and the second ball moves inwardly until it covers the throughbore in the eccentric valve seat to thereby prevent the back flow of fluid through the check valve assembly. During the pumping stroke, the pressure of the fluid urges the first ball outwardly until it rests against the face of the eccentric valve seat and the second ball moves outwardly against the face of the check valve fitting, to thereby provide fluid flow communication between the outlet passage in the cylinder head and the outlet passage in the check valve fitting. According to a feature of the invention, the concentric valve seat for the inlet check valve and the concentric valve seat for the outlet check valve are substantially identical, and the eccentric valve seat for the inlet check valve and eccentric valve seat for the outlet check valve are also substantially identical.

According to still another aspect of the invention, the cam face profile is shaped to synchronize the two top pistons for pumping and filling to minimize pressure pulsations and produce a substantially constant flow of fluid. In one form, the cam profile provides a parabolic rise, during rotation of the cam of from about 0° to about 30°, to drive the piston in such a manner as to create a hydraulic pulse which properly seats the check balls. Further, during rotation of the cam from between about 250° to about 345°, a cycloidal return gives a smooth piston retraction, which provides adequate cylinder refill time for a relatively high flow rate setting such as, for example, of the order of about 30 ml/min. In addition, a 15° dwell at the end of the cycloidal retraction is used to assure complete cylinder refill.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as the basis for the designing of other structures for carrying out the several purposes of the invention. It is important, therefore, that the claims be regarded as including such equivalent structures as do depart from the spirit and scope of the invention.

A specific embodiment of the invention has been chosen for purposes of illustration and description, and is shown in the accompanying drawings, forming a part of the specification.

BRIEF DESCRIPTION OF THE DRAWINGS

FIG. 1A is a side elevation, partially broken away, to show the lubrication system for the cam face;

FIG. 1B is an enlarged fragmentary view of the piston assembly;

FIG. 3A is an enlarged fragmentary sectional view of the high-pressure seal;

FIG. 4 is an enlarged plan view of the cam profile;

FIG. 5 is a chart setting forth the cam follower displacement equations for various degrees of cam rotation;

FIG. 6 is a diagram showing the cam follower displacement;

DETAILED DESCRIPTION OF THE PREFERRED EMBODIMENTS

Figure 1:
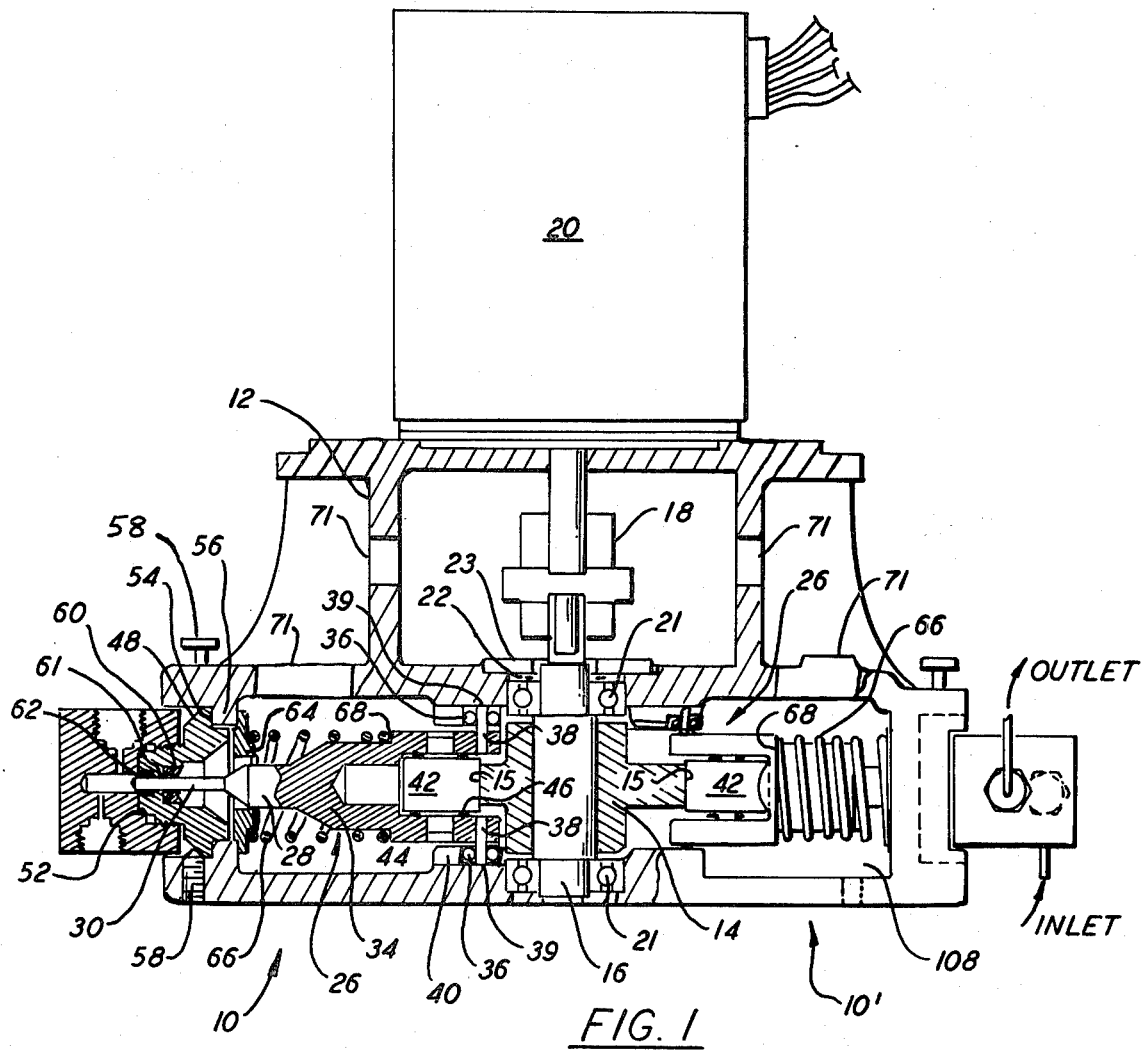
FIG. 1 is a plan view, partially broken away, showing a dual-piston reciprocating pump assembly constructed in accordance with the concepts of the invention.

The dual-piston reciprocating pump assembly illustrated comprises two opposed substantially identical reciprocating pumps, indicated generally at 16 and 10'. The pumps are mounted in an anodized aluminum housing 12 having a Teflon coating called Tufram which prevents corrosion from solvents and provides a low coefficient of friction surface for sliding members. The Teflon coating is diffused and bonded into the crystalline structure of the hard anodized aluminum. Interposed between the two pumps is a cam 14 mounted on a cam shaft 16, which is driven through a flexible coupling 18 by a stepper motor 20. The cam shaft is mounted on bearings 21 held in place in the housing 12 by a wave spring 22 and cover 23. Lubrication of the cam face is provided by a lubricated felt pad 24, FIG. 1A, carried on a wiper spring 25 mounted in cantilever fashion on the bottom cover 27, as at 29, for engaging the cam face 15 of the cam 14.

Figure 2:
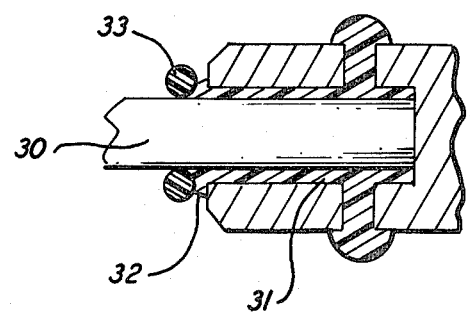
FIG. 2 is an enlarged, medial, sectional view showing the interconnection of the sapphire piston and the piston body.

Each pump includes a piston assembly 26, FIG. 1B, which comprises a piston body 28 having a sapphire piston end 30 fixedly connected thereto, as by means of suitable epoxy bonding material 31, FIG. 2. Sufficient bonding material can be used to form a head, as indicated at 32, and a Teflon O-ring 33 is mounted on the piston 30 adjacent the bead. Reverting to FIG. 1B, the other end of the piston body 28 is in the form of a yoke 34, which is mounted for reciprocating motion in the housing 12 by means of ball bearings 36 carried on piston bearing dowel pins 38 extending from the arms of the yoke, respectively. As seen in FIG. 1, the ball bearings 36 ride in slots 40 in the housing 12. A spherical cam roller bearing or cam follower 42 is carried between the arms of the yoke 34 by a dowel pin 44, and the shims 46 serve to reduce axial play between the yoke and the cam follower.

It will be appreciated that the piston design is such that friction forces are minimized on the piston during the pumping operation. The piston ball bearings 36, which ride in the slots in the pump housing share the loading created by the vertical component of the cam force. The piston bearings also prevent piston rotation, thereby providing adequate alignment of the cam follower 42 with the cam face 15 of the cam 14. The location of the bearing 36 on the piston is such that the moment (or couple) action on the piston by the vertical component of the cam during operation is minimized, thereby reducing the load on the sapphire piston end 30. The piston bearing dowel pins 38 have spherical ends 39, which are designed to transmit the cam side component of force to the pump housing 12. The pins slide against a low coefficient of friction surface of Tufram, which is plated on the aluminum pump housing.

Figure 3:
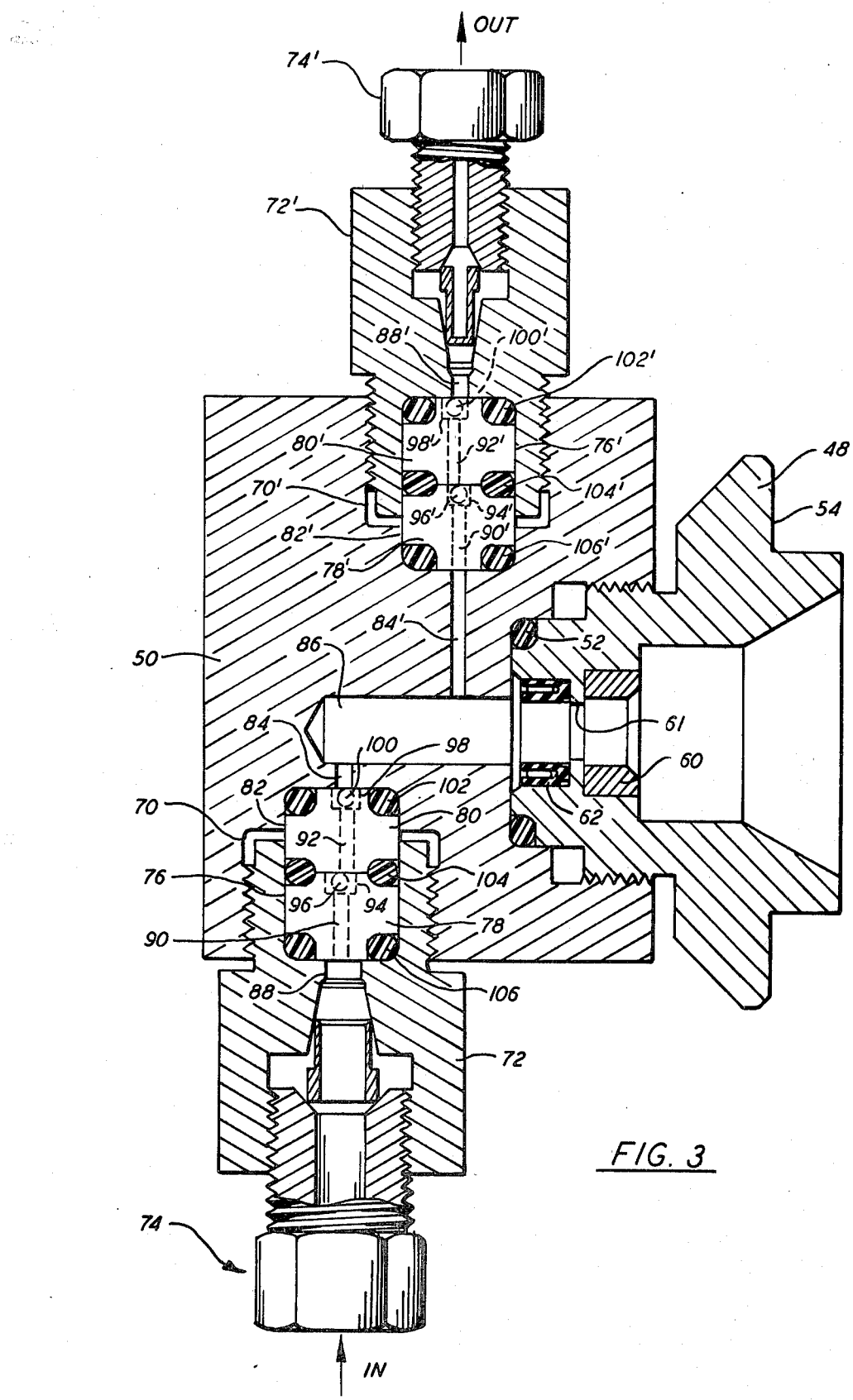
FIG. 3 is an enlarged, medial, sectional view showing the cylinder head, inlet check valve and outlet check valve.

As best seen in FIG. 3, a cylinder head 50 having an elongated piston cylinder 86 is provided for receiving the sapphire piston 30. A stainless steel seal holder 48 is threadably connected to the cylinder head 50 and is sealed with respect thereto by a Teflon "O" ring 52, provided for the purpose. The seal holder 48 has a shoulder 54 for engaging a radially-inwardly projecting, annular, mating shoulder 56, FIG. 1, in the housing 12. Thus, during assembly, the cylinder head 50 is mounted in an end opening in the housing 12 and is moved longitudinally inwardly until the shoulder 54 engages the shoulder 56, where it is secured in position by set screws 58. As seen in FIG. 3, the seal holder 48 has a longitudinally stepped bore for receiving a polytetrafluoroethylene or Teflon guide bushing 60, which acts as a guide or pilot for the sapphire piston 30 during assembly and disassembly of the unit. The seal holder 48 has an inner bearing bore or annular bearing surface 61, which acts as a metal bearing for the sapphire piston 30. The radial clearance between the bearing bore and the sapphire piston is the range of from about 0.0003 inches to about 0.00065 inches. A high-pressure fluorocarbon seal, indicated generally at 67, is mounted adjacent the inner bearing bore 61.

As seen in FIG. 3A, this seal includes an annular flexible sealing ring 63 having an annular wiper lip 65 and an annular backup lip 67. Between the two lips, a coiled spring 69 extends circumferentially around the piston 30 to thereby urge the wiper lip against the piston end and the backup lip against the seal holder 48. As viewed in cross-section, the backup lip 67 is of generally arcuate configuration whereas the wiper lip is shorter, straight and initially engages the piston along an end edge at the high pressure side thereof to thereby wipe the piston and prevent entry of foreign material or particles. The two lips face the high-pressure side of the seal so that the pressure tends to spread the lips and enhance the sealing action.

It will be appreciated that breakage of the sapphire piston is a serious problem for prior art reciprocating pumps of this nature, but this problem is substantially reduced by virtue of the structure of the present invention. The sapphire piston of the present invention is provided with radial end play in the range of from about 0.052 inches to about 0.0728 inches and, as a result, excessive piston side loading is avoided during cylinder assembly and disassembly. This radial end play enables the metal bearing bore 61 to be placed immediately adjacent the high-pressure seal 62, thereby preventing excessive side loading on the seal. The radial end play concept enables the piston to move to the actual physical center of the metal bearing and high-pressure seal, whereby the piston is adaptable to the tolerance of the pump parts and is not required to operate exactly on the piston theoretical centerline. Further, it will be appreciated that replacement of the high-pressure seal 62 can be effected quickly and easily, with little danger of breaking the sapphire piston during the seal replacement operation.

Reverting to FIG. 1, a spring holder 64 is mounted on the inner face of the shoulder 56 in the housing 12 for receiving one end of a piston spring 66. The piston body 28 has a shoulder 68 for receiving the other end of the spring 66. This spring serves to return the piston to its original position during the operation of the pump, as well as maintaining the cam follower 42 in engagement with the cam 14. As seen in FIG. 1, the housing 12 is provided with a plurality of vent slots 71 to allow corrosive vapors to escape out of and away from the pump internal parts. It will be appeciated that the piston slides into and out of a solvent stream and, hence, the vapors therefrom are particularly corrosive.

As best seen in FIG. 3, the cylinder head 50 also serves as a check valve body. The cylinder head is provided with an inlet bore 70 for threadably receiving a check valve fitting 72. The check valve fitting is adapted to receive a conventional end connection 74 of the pump inlet tube. The inner end of the check valve fitting 72 is provided with a recess 76 for receiving concentric valve seat 78 and an eccentric valve seat 80 mounted in series with respect to each other. In the pump inlet check valve, the eccentric seat 80 partially resides in a recess 82 at the bottom of the bore 70 in the cylinder head. The cylinder head 50 has an inlet passage 84 extending from the outer end of the piston cylinder 86 to the bottom of the recess 82. The check valve fitting 72 has an inlet passage 88, which is in alignment with the inlet passage 84, and the concentric valve seat 78 is provided with a throughbore 90, which is in alignment with the passage 84 as well as with the passage 88. The eccentric valve seat 80 is provided with a throughbore 92 that is slightly off-center with respect to the passage 84 and the throughbore 90, but is close enough thereto to provide fluid flow communication. The end of the throughbore 90 adjacent the valve seat 80 is provided with an enlarged portion 94 for loosely receiving a check valve ball 96 which may, for example, be fabricated of synthetic ruby. The end of the throughbore 92 adjacent the inlet passage 84 in the cylinder head 50 is provided with an enlarged portion 98 for loosely receiving a check valve ball 100 which also may, for example, be fabricated of synthetic ruby. In operation, when fluid is flowing inwardly through the inlet to the piston cylinder 86, the ball 96 moves inwardly and rests against the side face of the eccentric valve seat 80 and, at the same time, the ball 100 moves inwardly against the face of the cylinder head 50 adjacent the inlet passage 84, thereby providing fluid flow communication between the inlet passage 80 and the inlet passage 84. When the fluid flow is in the opposite direction, as during the pumping stroke of the reciprocating pump, the pressure of the fluid urges the ball 100 outwardly until it covers the inlet of the throughbore 92 and at the same time moves the ball 96 outwardly until it covers the throughbore 90, thereby preventing the flow of fluid through the check valve assembly.

The outlet check valve is similar to the inlet check valve so that the pair of check valve seats employed for the inlet check valve are interchangeable with the pair of valve seats utilized for the outlet check valve, by reversing the order in which they are mounted. The cylinder head 50 is provided with an outlet bore 70' for threadably receiving a check valve fitting 72'. The check valve fitting is adapted to receive a conventional and connection 74' of the pump outlet tube. The inner end of the check valve fitting 72' is provided with a recess 76' for receiving a concentric valve seat 78' and an eccentric valve seat 80' mounted in series with respect to each other. in the pump outlet check valve, the concentric seat 78' partially resides in a recess 82' at the bottom of the bore 70' in the cylinder head. The cylinder head 50 has an outlet passage 84' extending from the inner end of the piston cylinder 86 to the bottom of the recess 82'. The check valve fitting 72' has an outlet passage 88' which is in alignement with the outlet passage 84', and the concentric valve seat 78' is provided with a throughbore 90', which is in alignment with the outlet passage 84' as well as with the outlet passage 88'. The eccentric valve seat 80' is provided with a throughbore 92' that is slightly off-center with respect to the outlet passage 84' and the throughbore 90', but is close enough thereto to provide fluid flow communication. The end of the throughbore 90' adjacent the valve seat 80' is provided with an enlarged portion 94' for loosely receiving a check valve ball 96' which also may, for example, be fabricated of synthetic ruby. The end of the throughbore 92' adjacent the check valve fitting 72' is provided with an enlarged portion 98' for loosely receiving a check valve ball 100' which also may, for example, be fabricated of synthetic ruby. In operation, when the fluid is flowing outwardly through the outlet passage from the piston cylinder 86, the ball 96' is urged outwardly to rest against the valve seat 80' and, at the same time, the ball 100' is urged outwardly to engage the surface of the check valve fitting 72' thereby providing fluid flow communication between the outlet passage 84' and the outlet passage 88'. During the intake stroke of the reciprocating pump, the back pressure on the discharge line urges the ball 100' inwardly to close the outer end of the throughbore 92' and, at the same time, urges the ball 96' inwardly to close the throughbore passage 90', thereby preventing fluid flow through the check valve assembly.

To prevent leakage at the interface between the cylinder head 50 and the valve seat 80 an O-ring 102 is provided adjacent the periphery of the valve seat, and to prevent leakage at the interface between the valve seat 80 and the valve seat 78 an O-ring 104 is provided at the periphery of the valve seats. An O-ring 106 serves to prevent leakage between the valve seat 79 and the check valve fitting 72. In a similar manner, O-ring 102' provides a seal at the interface between the check valve fitting 72' and the valve seat 80', while an O-ring 104' serves to provide a seal between the valve seat 80' and the valve seat 78'. An O-ring 106' provides sealing between the valve seat 78' and the cylinder head 50. Thus, these O-ring seals prevent flow circulation from occurring within the check valves.

Preferably, in installations utilizing common liquid chromatography solvents, the check valve seats are fabricated from stainless steel type 316 which is chemically resistant to such solvents. Moreover, each individual check valve seat can be replaced, if necessary, without replacing the entire assembly.

It will be particularly appreciated that the two-stage inlet check valve as well as the two-stage outlet check valve just described, are so constructed as to reduce the retention of trapped gas (air) and trapped liquids in the pump cylinder head. This is due to the fact that the inlet passage 84 is offset with respect to the outlet passage 84' in the cylinder head, thereby providing a flow-through or flushing action in the piston cylinder, which prevents the retention of trapped fluids.

As best seen in FIG. 1, the pump mechanical parts can be viewed through a glass cover 108, which enables the operator to see and correct mechanical problems.

Figure 7:
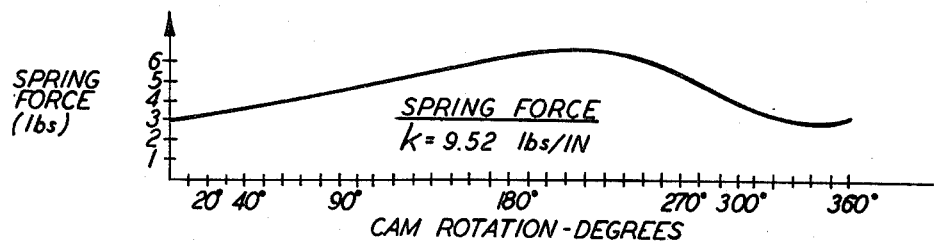
FIG. 7 is a spring force diagram.

FIG. 4 shows the cam surface 15 on the cam 14, which is keyed to the cam shaft 16. The profile of the cam face 15 of the cam 14 is defined by the four mathematical equations, as indicated on the chart, FIG. 5, wherein:

$y$ = follower displacement
$h$ = follower displacement for 30° of cam rotation
$h_1$ = follower displacement for 180° of cam rotation
$h_2$ = follower displacement for 210° of cam rotation (max. displacement for entire cycle)
$h = h_2 - h_1$
$\theta$ = cam angle of rotation for a follower displacement $y$, in degrees This synchronises the pumping and filling actions of the dual pistons to produce a constant flow with a minimum of pulsation. The parabolic rise in the pump cycle for a cam rotation of from about 0° to about 30° is designed to drive the piston in such a manner as to create a hydraulic pulse, which properly seats the check balls in the check valve. The cycloidal piston return of about 130° of cam rotation gives a smooth piston retraction, which provides adequate cylinder refill time for relatively high nominal flow settings such as about 30 ml/min., for example. The 15° dwell at the end of the cycloidal retract is used to assure complete cylinder refill. The cam follower displacement diagram, FIG. 6, shows the relationship of the cam rotation in degrees with respect to the cam follower or piston displacement in inches. FIG. 7 is a spring-force diagram showing the relationship between the cam rotation in degrees and the force of the spring 66 in pounds. In this illustrative embodiment, the spring has a spring constant of 9.52 pounds per inch and an initial deflection of 0.35 inches.

Figure 8:
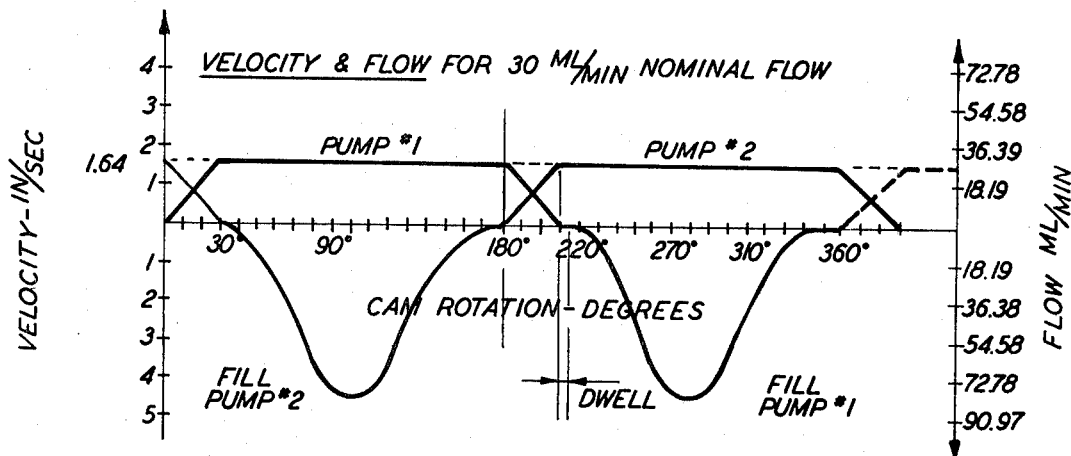
FIG. 8 is a pump velocity and flow diagram.
Figure 9:
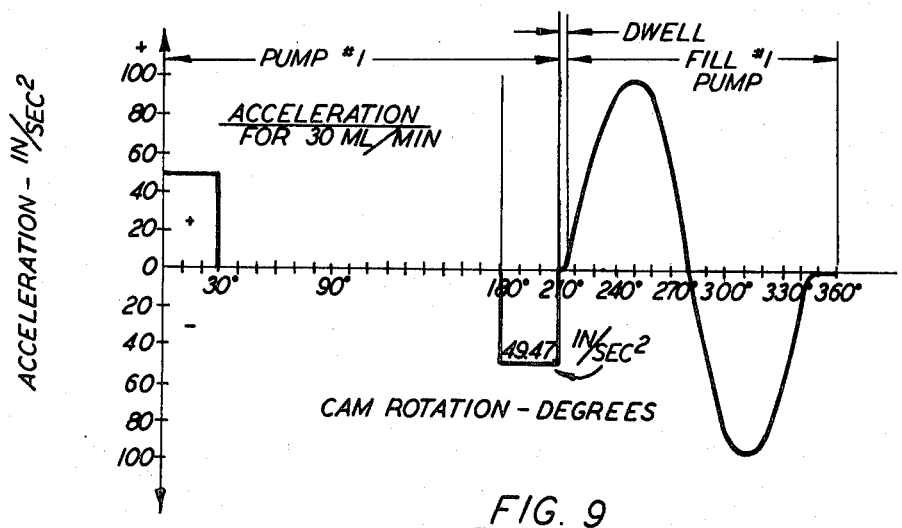
FIG. 9 is a cam follower acceleration diagram.

FIG. 8 shows a velocity and flow diagram for a nominal 30 ml/min. capacity pump assembly. FIG. 9 is an acceleration diagram showing the piston acceleration with respect to the cam angle in degrees for the dual piston reciprocating pump assembly, according to the invention, having a nominal capacity of 30 ml/min.

It will thus be seen that when the cam 14 is rotated by the stepper motor 20 at uniform angular velocity, the cam's prescribed motion imparts a prescribed motion to the two pistons or followers. This dual-piston system allows one chamber to fill while the other piston provides flow to the system. The cam is designed to synchronize the pistons for pumping and filling in such a way as to minimize pressure pulsations and produce a relatively constant flow of solvent to the liquid chromatography system.

From the foregoing description, it will be seen that the present invention does indeed provide a new and improved dual-piston reciprocating pump assembly, which is capable of delivering constant flow at low flow rates for analytical chromatography and at high flow rates for small scale preparative chromatography, the high flow rate capability also enabling the fast system flushing for solvent changeover. In addition, the pump assembly according to the present invention is superior in simplicity, operability, reliability and efficiency as compared to prior art such devices.

Having thus described the invention with particular reference to the preferred forms thereof, it will be obvi- ous to those skilled in the art to which the invention pertains, after understanding the invention, that various changes and modifications may be made therein without departing from the spirit and scope of the invention, as defined by the claims appended hereto.

What is claimed is:

1. A dual-piston reciprocating pump assembly comprising two opposed substantially identical reciprocating pumps, a housing in which said pumps are mounted, a motor, a flexible coupling, a cam shaft, and a cam, said cam being mounted on the cam shaft which is driven through the flexible coupling by the motor, the cam face of said cam being contoured to produce a piston displacement with respect to cam angle according to the following:

| CAM ROTATION | FOLLOWER DISPLACEMENT EQUATION |
|---|---|
| 0°–30° | $y = 4h\left(\dfrac{\theta}{60°}\right)^2$ |
| 30°–180° | $y = h + \dfrac{(h_1 - h)(\theta - 30°)}{150°}$ |
| 180°–210° | $y = 2h\left\{1 - 2\left[1 - \dfrac{(\theta - 150°)}{60°}\right]^2\right\} + h_1 - h$ |
| 210°–215° | $y = h_2$ dwell (continuous maximum displacement) |
| 215°–345° | $y = h_2 - \left\{\dfrac{h_2}{\pi}\left[\dfrac{\pi(\theta - 215°)}{130°} - \tfrac{1}{2}\sin\dfrac{2\pi(\theta - 215°)}{130°}\right]\right\}$ |
| 345°–360° | $y = 0$ dwell (continuous no displacement) | where:
$y$ = follower displacement
$h$ = follower displacement for cam rotation of 30°
$h_1$ = follower displacement for cam rotation of 180°
$h_2$ = follower displacement for cam rotation of 210° (maximum displacement for entire cycle)
$\theta$ = cam angle of rotation for a follower displacement $y$, in degrees, 2. A dual-piston reciprocating pump assembly according to claim 1 wherein:

$h = h_2 - h_1$.

3. A dual-piston reciprocating pump assembly comprising two opposed substantially identical reciprocating pumps, a housing within which said pumps are mounted, a motor, a coupling, a cam shaft, and a cam, said cam being mounted on the cam shaft which is driven through the coupling by the motor, each of said reciprocating pumps including a piston assembly comprising a piston body having a piston end, a cam follower mounted on the other end of the piston body for engaging the cam face of said cam, each of said reciprocating pumps having a piston cylinder for receiving its piston end, each piston cylinder having an inlet and an outlet and each inlet and outlet having a check valve, thereby forming means for alternately pulling fluid into the piston cylinder and pushing fluid out of the piston cylinder, the cam face of said cam being contoured to provide a follower displacement with respect to cam angle during cam rotation, said cam face having six distinct cam surfaces, the first cam surface being contoured to provide a parabolic rise, the second cam surface being contoured to provide a linear rise, the third cam surface being contoured to provide a parabolic rise, the fourth cam surface being contoured to provide a continuous maximum displacement dwell, the fifth cam surface being contoured to provide a cycloidal return and the sixth cam surface being contoured to provide a continuous no displacement dwell.

4. A dual-piston reciprocating pump assembly according to claim 3 wherein said cam is a radial type cam and said six cam surfaces correspond to degrees of cam rotation as follows:

first cam surface is from about 0 degrees to about 180 degrees, second cam surface is from about 35 degrees to about 180 degrees, third cam surface is from about 180 degrees to about 210 degrees, fourth cam surface is from about 210 degrees to about 215 degrees, fifth cam surface is from about 215 degrees to about 345 degrees, sixth cam surface is from about 345 degrees to about 360 degrees.

* * * * *